(12) United States Patent
Yamada et al.

(10) Patent No.: US 8,685,278 B2
(45) Date of Patent: Apr. 1, 2014

(54) FLUORESCENT ZIRCONIA MATERIAL

(75) Inventors: Yoshihisa Yamada, Miyoshi (JP); Yoshihisa Ito, Miyoshi (JP)

(73) Assignee: Noritake Co., Limited, Aichi (JP)

( * ) Notice: Subject to any disclaimer, the term of this patent is extended or adjusted under 35 U.S.C. 154(b) by 0 days.

(21) Appl. No.: 13/258,865

(22) PCT Filed: Mar. 17, 2010

(86) PCT No.: PCT/JP2010/054610
§ 371 (c)(1), (2), (4) Date: Sep. 22, 2011

(87) PCT Pub. No.: WO2010/110156
PCT Pub. Date: Sep. 30, 2010

(65) Prior Publication Data
US 2012/0012789 A1    Jan. 19, 2012

(30) Foreign Application Priority Data
Mar. 23, 2009 (JP) ................................. 2009-070990

(51) Int. Cl.
C09K 11/08    (2006.01)
C09K 11/66    (2006.01)

(52) U.S. Cl.
USPC ................................................. 252/301.4 F

(58) Field of Classification Search
USPC ........ 252/301.4 R, 301.5 R, 301.6 S, 301.6 F, 252/301.4 S, 301.4 F; 501/103, 152
See application file for complete search history.

(56) References Cited

U.S. PATENT DOCUMENTS

| | | | |
|---|---|---|---|
| 3,984,524 A * | 10/1976 | Alexandrov et al. ......... 423/266 | |
| 5,263,858 A | 11/1993 | Yoshida et al. | |
| 6,709,694 B1 | 3/2004 | Suttor et al. | |
| 6,713,421 B1 * | 3/2004 | Hauptmann et al. .......... 501/103 | |
| 2003/0124383 A1 * | 7/2003 | Akiyama et al. .............. 428/690 | |
| 2003/0145525 A1 * | 8/2003 | Rosenflanz ..................... 51/307 | |
| 2005/0209082 A1 | 9/2005 | Apel et al. | |
| 2006/0261503 A1 * | 11/2006 | Sago et al. ....................... 264/16 | |
| 2007/0063155 A1 * | 3/2007 | Fukui .......................... 250/484.4 | |
| 2007/0182042 A1 | 8/2007 | Ikushima et al. | |
| 2008/0303181 A1 * | 12/2008 | Holand et al. ................... 264/16 | |
| 2008/0318757 A1 * | 12/2008 | Fotou et al. ...................... 501/29 | |
| 2009/0009059 A1 * | 1/2009 | Kwon et al. ................... 313/503 | |
| 2009/0202864 A1 * | 8/2009 | Feist et al. .................... 428/690 | |

FOREIGN PATENT DOCUMENTS

| | | |
|---|---|---|
| DE | 10 2009 030 951 A1 | 1/2010 |
| JP | A-3-200891 | 9/1991 |
| JP | A-10-36137 | 2/1998 |
| JP | A-2000-256591 | 9/2000 |
| JP | A-2003-171662 | 6/2003 |
| JP | A-2004-292588 | 10/2004 |
| JP | A-2005-34275 | 2/2005 |
| JP | A-2005-53776 | 3/2005 |
| JP | A-2005-263627 | 9/2005 |
| JP | A-2007-210822 | 8/2007 |
| JP | A-2007-314536 | 12/2007 |
| JP | A-2010-047460 | 3/2010 |

OTHER PUBLICATIONS

Huangqing et al., "Effect of Annealing Temperature on Luminescence of Eu3+ Ions Doped Nanocrystal Zirconia" Applied Surface Science, Feb. 1, 2007, vol. 253, pp. 3872-3876.*
International Search Report mailed Apr. 27, 2010 issued in International Patent Application No. PCT/JP2010/054610 (with translation).
Dec. 27, 2011 European Search Report issued in European Patent Application No. 10755954.4.
W.A. Hollerman et al., "Development of Fluorescent Coatings for High Temperature Aerospace Applications," Jan. 1, 2002, pp. 1-10.
Zhiqiang Ye et al., "Preparation, Characterization and Application of Fluorescent Terbium Complex-Doped Zirconia Nanoparticles," Journal of Fluorescence, Jul. 1, 2005, vol. 15, No. 4, pp. 499-505.
Liu Huangqing et al., "Effect of Annealing Temperature on Luminescence of Eu$^{3+}$ Ions Doped Nanocrystal Zirconia," Applied Surface Science, Feb. 1, 2007, pp. 3872-3876, vol. 253.
May 27, 2013 Second Notification of Reasons for Rejections issued in Chinese Application No. 201080022443.0 with English-language translation.
Apr. 2, 2013 Japanese Office Action issued in Japanese Application No. 2009-070990 with partial English-language translation.
Huangqing et al., "Effect of Annealing Temperature on Luminescence of Nano Material ZrO2: Eu3+ Ion," Acta Physica Sinica, vol. 56, No. 1, pp. 556-560, 2007, with English-language Abstract.
Dec. 10, 2013 Third Notification of Reasons for Rejection issued in Chinese Application No. 201080022443.0 with English-language translation.

* cited by examiner

Primary Examiner — Emily Le
Assistant Examiner — Lynne Edmondson
(74) Attorney, Agent, or Firm — Oliff PLC

(57) ABSTRACT

It is provided a fluorescent zirconia material including a fluorescent component and emitting fluorescence when excited with a light of a predetermined wavelength, the fluorescent component including a fluorescent material, the fluorescent material including at least one kind of $Y_2SiO_5$:Ce, $Y_2SiO_5$:Tb, (Y, Gd, Eu)$BO_3$, $Y_2O_3$:Eu, YAG:Ce, $ZnGa_2O_4$:Zn and $BaMgAl_{10}O_{17}$:Eu and the fluorescent material being capable of emitting the fluorescence when subjected to firing treatment at temperatures ranging from 1300 to 1600(° C.) under oxidizing environments.

3 Claims, 2 Drawing Sheets

US 8,685,278 B2

FLUORESCENT ZIRCONIA MATERIAL

FIELD OF THE INVENTION

This invention relates to fluorescent zirconia materials for giving fluorescence emission when excited with predetermined wavelengths.

BACKGROUND OF THE INVENTION

When fabricating a dental prosthesis to be mounted in a mouth, for instance, it has been a practice to cut out a block, composed of zirconia (zirconium oxide), to form a frame for use using CAD/CAM techniques (see, for example, Patent Publication 2). Employing such a frame made of zirconia enables a whole of the prosthesis to be formed of ceramic in all-ceramic material. This provides advantages of addressing or alleviating various issues. These include metal allergy arising from the prosthesis, having metal applied to a surface of a metal frame for covering ceramic material (porcelain material) for adjusting a color tone into a natural tooth to be in contact with a body; and a difficulty of getting color tones of natural teeth in nature due to an unclear undercoat layer provided for concealing a metal color.

PUBLICATIONS ON PRIOR ART

Patent Publications
Patent Publication 1: Japanese Patent Application Publication 10-036137
Patent Publication 2: Japanese Patent Application Publication 2005-053776
Patent Publication 3: Japanese Patent Application Publication 2007-314536

SUMMARY OF THE INVENTION

Problems to be Solved by the Invention

Meanwhile, the zirconia block has been conventionally provided to a dental laboratory or a dental technician in the form of an unburned compact body, a calcined body subjected to calcining treatment or a sintered body subjected to firing treatment. According to a model prepared by a dental doctor, then, the dental laboratory or the dental technician fabricates a prothesis by fabricating a frame from the block and building up porcelain on the frame. With expansion in market of zirconia-based tooth crown frames progressively spreading in dental business, by the way, there occurs a situation in which cheap pirated zirconia blocks are used in part.

Presence of such pirated materials cannot be ignored for a source of supply of proper products. Particularly, it has been desired to have a capability of checking out a source of origin in association with a warranty to be given in preparation to the occurrence of damage caused by a drop in strength of the tooth crown frame with no matching to design value. However, since the prosthesis is fabricated in such a process noted above, no external appearance of the prosthesis provides characteristics peculiar to the source of origin of the zirconia block. Therefore, difficulties are encountered not only for the suppliers of the proper products but also for the dental doctors to check out the source of origin of the zirconia block used for the prosthesis. This makes the pirated blocks easier to be used.

Although the issues, mentioned above, are related to the zirconia frame used for the dental prosthesis, such issues are not limited to the dental prosthesis. For instance, it is similarly desired to have a capability of checking out sources of origins even in association with zirconia ceramics in various forms provided in mechanical devices or the like as replacement repair parts or the like if it is supposed that pirated replacement repair parts may be used and get damaged. That is, the checking of the source of origin is not limited to the zirconia block used for the dental prosthesis and sources of origins for used materials have been desired to be checked out especially when encountered with the occurrence of damages, i.e., a traceability function has been desired to be given.

Upon various studies being conducted by the present inventors, it have been found to be appropriate for the zirconia material to have fluorescent property in order to have the traceability function. The present invention has been completed with the above finding and has an object to provide a zirconia material that provides fluorescence emission.

Means for Solving the Problem

The object indicated above can be achieved according to one aspect of the present invention, which provides a fluorescent zirconia material including a fluorescent component and emitting fluorescence when excited with a light of a predetermined wavelength.

Effects of the Invention

With such a feature, the zirconia material can be obtained in inclusion of a fluorescent component to have a fluorescent property. Therefore, irradiating a light with the predetermined wavelength, allows the zirconia material to emit fluorescence, resulting in the provision of the traceability function regardless of applications of the dental materials and structural materials or the like. In addition, especially, suitably selecting relevant exciting wavelengths and fluorescent colors allows the dental materials to have an increased esthetical effect.

Accordingly, when the present invention is applied to the dental zirconia block for the frame, etc., to be fabricated by, for instance, CAD/CAM, checking out fluorescence of a broken surface, when encountered damage to at least a dental prosthesis, allows a determination to be easily made as to whether the relevant product belongs to a proper one. Moreover, when applied to the structural materials or the like, a determination can be easily made, when encountered damage to a component part, as to whether the component part belongs to a proper product. Even in a case where a broken component part is mixed to a treated material or the like, irradiating a light at an exciting wavelength results in a capability of checking the presence or the absence of such a mixed state.

With the present invention, further, examples of the zirconia material may include a raw material, a green compact body not subjected to heat treatment, a calcined body subjected to degreasing and calcining treatments and a sintered body subjected to firing treatment in any shapes.

In this connection, when the dental prosthesis has been fabricated in the related art, it has been a practice to add the fluorescent material to the porcelain material to be modeled (built up) on the surface of the frame (see, for instance, Patent Publication 1). This is intended to allow the frame to have a color tone matched to the natural tooth having a slight degree of fluorescent property as close as possible. Thus, no consideration is made on the traceability and no attempt is made to think about giving fluorescent property to the frame material.

Further, various attempts have heretofore been made in the related art to give coloring to a whole of the dental prosthesis inclusive of the frame (see, for instance, Patent Publications 2 and 3). It has been known for metal oxides, having fluorescent property, to be added in such an object. However, no finding has been made as to what kind of fluorescent property is owned by the metal oxides being added and as to whether the frame has fluorescent property even after the completion of firing treatment and no consideration has been made on traceability.

Preferably, the predetermined wavelength is a wavelength of ultraviolet rays equal to or greater than 300 (nm) with the fluorescence being provided in blue color and blue-white color. With such features, the zirconia material can have fluorescent property that emits fluorescence in colors from blue to blue white with a short wavelength range of a visible light or a wavelength range slightly deviated therefrom on a side closer to ultraviolet rays. Due to the presence of fluorescent property proximate to the natural tooth, therefore, the present invention can be preferably applied to the frame of the dental prosthesis and brackets of an orthodontic bracket, etc., thereby obtaining a dental prosthesis and a bracket with excellent esthetical effects.

In this connection, it has been desired for the dental prosthesis to have texture resembled to the natural tooth as close as possible in terms of esthetical effects. For the orthodontic bracket, a zirconia-based bracket has been employed in place of metal-based one in recent years. Since the zirconia-based bracket is fixed to a surface of the tooth, like the dental prosthesis, it has been desired for the zirconia-based bracket to have texture resembled to the natural tooth as close as possible.

Preferably, the predetermined wavelength is a wavelength of ultraviolet rays equal to or less than 300 (nm). With such features, since the excitation wavelength is sufficiently shorter than the visible light, no emission of fluorescence occurs in a light received by a human body in daily life. When applied to the dental prosthesis, therefore, even if it emits fluorescence different in color from that of the natural tooth, fluorescence has no adverse affect on the esthetical effect in daily life. Meanwhile, irradiating the ultraviolet rays of a wavelength equal to or less than 300 (nm) enables fluorescence to be observed, thereby making it possible to obtain a dental prosthesis with the provision of a traceability function without sacrificing any esthetical effect.

Preferably, the fluorescent component includes a fluorescent material that can emits the fluorescence when subjected to firing treatment at temperatures ranging from 1300 to 1600(° C.) under oxidizing environments. The fluorescent property of the zirconia material can be afforded with the fluorescent material that can emit fluorescence even when subjected to firing treatment at such high temperatures. When fabricating, for instance, the zirconia material, the fluorescent material can be mixed in the form of fluorescent powder to the raw material powder.

In the above embodiment, the fluorescent material includes at least one kind of $Y_2SiO_5$:Ce, $Y_2SiO_5$:Tb, (Y, Gd, Eu)$BO_3$, $Y_2O_3$:Eu, YAG:Ce, $ZnGa_2O_4$:Zn and $BaMgAl_{10}O_{17}$:Eu. Although the present invention has no specific limitation on the fluorescent materials that provide the zirconia material with fluorescent property, the fluorescent property can be provided in an appropriate degree when these fluorescent materials, for instance, are used.

$Y_2SiO_5$:Ce is one of those, which has been known to be a blue-colored fluorescent substance, and emits a light in blue color when excited with the ultraviolet rays. However, even when it is added with the zirconia material, the zirconia material can sustain a body color in nearly white color with a color tone having no particular variation. The addition of such material of about 1 (wt %) results in a loss of fluorescent property when fired at high temperatures equal to or greater than 1400(° C.), for instance. However, adjusting the added amount to be equal to or greater than, for instance, 3 (wt %) enables the fluorescent property to be sustained for thereby providing the traceability function and enables the use for affording an esthetical effect closer to that of the natural tooth.

Further, $Y_2SiO_5$:Tb is fluorescent substance that emits a light in green color when excited with the ultraviolet rays but allow the zirconia material to have a color tone varied in light orange color. Therefore, it is hard to utilize such substance as the dental material in a way where relevant fluorescence appears on the outside. However, such a substance can be used as the dental material in an application where fluorescence of the frame cannot be observed such as for forming a frame whose surface is provided with a porcelain material in adequate thickness and it doesn't matter if used for a structural material.

Furthermore, (Y, Gd, Eu)$BO_3$ and $Y_2O_3$:Eu are fluorescent substances that emit lights in pink color when excited with the ultraviolet rays and has adequately high brightness with no likelihood of adversely affecting a color tone of the zirconia material to be preferably used as the dental material. The additions of these substances of about, for instance, 3 (wt %) result in an effect of providing an adequate degree of fluorescent property.

Furthermore, $ZnGa_2O_4$:Zn is fluorescent substance that emits a light in blue color when excited with the ultraviolet rays and has adequately high brightness with no likelihood of adversely affecting a color tone of the zirconia material to be preferably used as the dental material.

Moreover, YAG:Ce is fluorescent substance that emits a light in green color when excited with the ultraviolet rays but allow the zirconia material to have a color tone varied in yellow color. Therefore, it is hard to utilize such substance as the dental material in which relevant fluorescence appears on the outside. However, such substance can be used as the dental material in the application where fluorescence of the frame cannot be observed such as for forming the frame whose surface is provided with porcelain material in adequate thickness and it doesn't matter if used for a structural material.

Furthermore, $BaMgAl_{10}O_{17}$:Eu is fluorescent substance that emits a light in blue color when excited with the ultraviolet rays and has adequately high brightness with no likelihood of adversely affecting a color tone of the zirconia material to be preferably used as the dental material.

Preferably, the fluorescent material includes at least one kind of element of Pr, Sm, Eu, Ga, Gd, Tm, Nd, Dy, Tb and Er or at least one kind of compounds of the element, wherein zirconium oxide per se has fluorescent property. With such elements being added, the zirconia material per se is provided with fluorescent property even though such occurrence cannot be confirmed to result from any kind of presence state. As set forth above, like the case in which the fluorescent material is added, the zirconia material can be obtained with fluorescent property.

In the above embodiment, the element is contained at a rate equal to or greater than 0.0001 (wt %). Even when added in an extremely small content, the various elements are capable of providing the zirconia material with fluorescent property and, hence, the content of such elements in an amount equal to or greater than 0.0001 (wt %) will be sufficient. Moreover, the emission of fluorescence becomes intensive as the content of such elements becomes great, but it is considered that when the addition of such elements exceeds at a ratio, strength becomes deteriorated. Upon various tests conducted by the present inventors, however, adding such elements in an amount up to 10 (wt %) resulted in a capability of maintaining of the strength at a level available to be used. Therefore, an upper limit of the content amounts is at least 10 (wt %). In order to obtain further increased brightness, the content may be preferably selected to be equal to or greater than 0.001 (wt %). In order to suppress a deterioration in strength caused by foreign materials being added, it is further preferable for the added amount to be kept in a range equal to or less than 5 (wt %).

Preferably, the element is added in the form of compounds $Pr_2O_3$, $Sm_2O_3$, $Eu_2O_3$, $Ga_2O_3$, $Gd_2O_3$, $Tm_2O_3$, $Nd_2O_5$, $Dy_2O_3$, $Tb_4O_7$ abd $Er(CH_3COO)_3$. The elements, set forth above, can be added in an appropriate mode unless otherwise no compound, such as oxides or acetate salts or the like caused by decomposition occurring during firing treatment, causes adverse affect on the characteristics. For instance, the compound may suffice to be hydrates. Further, when providing the zirconia material with fluorescent property, for instance, an attempt may be made to adopt a method in which the compound composed of such various elements mentioned above, is mixed with zirconia raw material powder and molded after which firing treatment is conducted or the like. By employing those of such an average particle diameter noted above, the compounds can be uniformly dispersed during mixing step, thereby making it possible to obtain highly uniformed zirconia material.

Among the various elements set forth above, further, the element of Eu may be especially preferred because the addition of Eu even in a small amount results in emission of a light in an intense orange color with no variation caused in color tone of the zirconia material. When adding, for instance, the oxide $Eu_2O_3$, the added amount may suffice to fall in a value of about 0.05 (wt %) and the brightness becomes high as the added amount becomes great. In an alternative, the firing condition may be modified, i.e., firing treatment may be conducted under reducing atmosphere such that fluorescence is emitted in, for instance, blue color.

Further, Sm, Ga, Gd, Tm and Nd, which are lower in brightness than that of Eu, allow the zirconia material to have fluorescence with no occurrence of variation in color tone. These elements result in emission of fluorescence in blue color even in the presence of weak emission of light.

Furthermore, Dy has an ability to provide fluorescent property without causing any change in color tone of the zirconia material. This results in emission of a light with high brightness when irradiated with the ultraviolet rays at a relatively long wavelength of about 365 (nm). Even though the emission occurs with the ultraviolet rays of about 254 (nm), there is a tendency in which the brightness is lower than that of the above wavelength. Thus, this element may preferably have applications where the inspection is conducted using a black light. In addition, the emission wavelength covers a wide range and the emission may be in blue color, but the strongest emission occurs in orange color, while emitting a light in light orange color as a whole.

Moreover, Pr, by which the zirconia material is colored in brown, emits fluorescence in orange color when excited with the ultraviolet rays at a wavelength region of about 254 (nm).

Besides, Tb, by which the zirconia material is colored in orange, emits a light in blue to orange colors with high brightness when excited with the ultraviolet rays at the wavelength of about 254 (nm).

In addition, Er, by which the zirconia material is colored in light pink, emits fluorescence but with low brightness when excited with the ultraviolet rays at wavelengths of about 254 (nm) and about 365 (nm).

With the present invention, further, the zirconia material may be applied in use with no particular limitations. The zirconia material has application to, for instance, frames of dental prostheses and orthodontic brackets, but this material is not limited to the dental use and may have applications to structural materials. When applied to the structural materials, for instance, the zirconia material of the present invention can be used for the purpose of finding the occurrence of a damaged component part being mixed to an object to be treated by using UV irradiation.

Furthermore, in any of cases where the fluorescent material is added or where the various elements are added in the form of oxides or the like, additives may be added in appropriate modes regardless of solid or liquid. A mixing method may be conducted in appropriate methods including dry mixing with the use of a mortar or wet mixing with the use of ball mills or the like.

Moreover, the zirconia material, to which the present invention can be applied, is not limited to particular crystalline systems. In any of applications to tetragonal systems and cubic systems, fluorescence can be provided.

Zirconia materials, to which the present invention can be preferably applied, may include, for instance, 91.00 to 98.45 (wt %) of zirconium oxide, 1.5 to 6.0 (wt %) of yttrium oxide, and at least one oxide of aluminum, gallium, germanium and indium in a range of 0.05 to 0.50 (wt %). Constituents of the zirconia material are not particularly limited with stabilizing agents including, for instance, in addition to yttrium oxide, cerium oxide, calcium oxide and magnesium oxide, etc. When used as, for instance, the dental material, the composition mentioned above may be preferred in terms of strength and color tone or the like.

More preferably, further, the zirconia material may include coloring agents, in addition to the fluorescent material, various elements and relevant compounds for providing fluorescent property. In applications to, for instance, the dental materials, it becomes possible to obtain an artificial tooth closer to a natural tooth in color tone even when encountered with a difficulty in the presence of a color tone of zirconium oxide in nature intact. Examples of coloring agents may include transition metal oxides in Groups 4 to 6, aluminum compounds, silicone compounds, iron oxides, magnesium oxide, nickel oxide, iron sulfide, magnesium sulfide, nickel sulfide, nickel acetate, iron acetate and magnesium acetate, etc. These coloring agents may be simultaneously added when organic bonding agents are added to the zirconia material for granulations, for instance. In addition, when performing the granulations, sintering additives may be added depending on needs.

BEST MODE FOR CARRYING OUT THE INVENTION

Now, one embodiment of the present invention will be described below in detail with reference to the accompanying drawings. Further, the embodiment, described below, is suitably simplified or modified in drawings with none of the parts being necessarily drawn precisely in dimension and shapes, etc.

Embodiment

Figure 1:
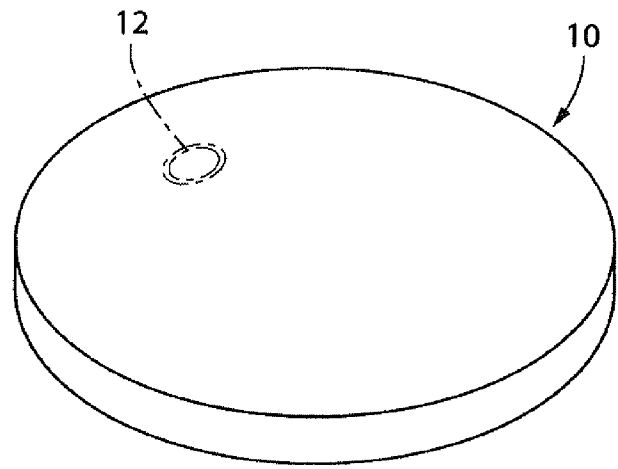
FIG. 1 is a view showing a disc-shaped zirconia block of one embodiment according to the present invention.

FIG. 1 is a perspective view showing a disc-shaped dental zirconia block 10. The block 10, formed of zirconia ceramic (TZP) made of, for instance, zirconium oxide to which 3 (mol %) of yttrium oxide was added as stabilizing agent, contains, for instance, europium oxide ($Eu_2O_3$) at a ratio of about 0.05 (wt %). Further, the block 10 includes a calcined body, composed of a compact body subjected to degreasing and calcining treatment at low temperatures in a manner as described later, which is formed in size with a diameter of approximately 94 (mm) and a thickness of about 14 (mm).

Figure 2:
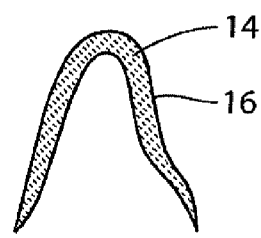
FIG. 2 is a view showing a cross-sectional structure of a single crown frame fabricated by cutting the zirconia block of FIG. 1.
Figure 3:
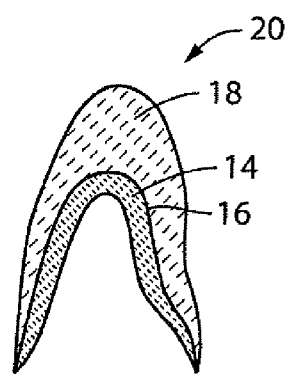
FIG. 3 is a view showing a cross-sectional structure of an artificial tooth with porcelain modeled on a surface of the single crown frame.

The block 10 is used as frames of all-ceramic prostheses such as, for instance, a bridge and a crown or the like. An exemplary outline of the frame to be cut out is shown in FIG. 1 by a single dot line 12 and one example of the prepared frame 14 is shown in FIG. 2 in cross section. The frame 14, shown in FIG. 2, has a surface 16 on which porcelain is modeled to form an upper layer 18, resulting in the formation of a tooth crown 20, as shown in FIG. 3, to be mounted on an upper anterior tooth of an adult.

Since the frame 14, fabricated from the block 10, contains $Eu_2O_3$ as mentioned above, the irradiation of ultraviolet rays at a wavelength of about 254 (nm), using an UV lamp in general use, results in emission of fluorescence in orange color. When irradiated with a black light at a wavelength of about 365 (nm), further, emission of fluorescence in blue color occurs. Due to the presence of the same fluorescent property as that of a natural tooth, therefore, the frame 14 has characteristics to have an esthetical effect further closer to that of the natural tooth than that obtained by a related art metal frame or a zirconia frame having no fluorescent property. With the tooth crown 20 made of the frame 14 on which the upper layer 18 is formed, no fluorescence emission could be observed in areas except for an area where the upper layer 18 is formed thinned even when similarly irradiated with the ultraviolet rays. That is, the frame 14 emits fluorescence under an exposed state but the emission hardly takes place when covered with the porcelain material. With the present embodiment, the frame 14 has fluorescent property closer to that of the natural tooth and it doesn't matter if the exposed area is present. For the concern described above, even if the frame is made of zirconia material different in fluorescent color, no issue will arise when covered with the upper layer 18 with an adequate thickness in dimension.

When the ultraviolet rays are irradiated, using the UV lamp, onto a broken surface of the frame 14 in an area exposed when the tooth crown 20 was cracked, furthermore, the emission of fluorescence was recognized in an orange color. That is, when, for instance, the tooth crown 20 is damaged in use, it becomes easy to confirm whether the frame 14, forming the tooth crown 20, emits fluorescence.

Figure 4:
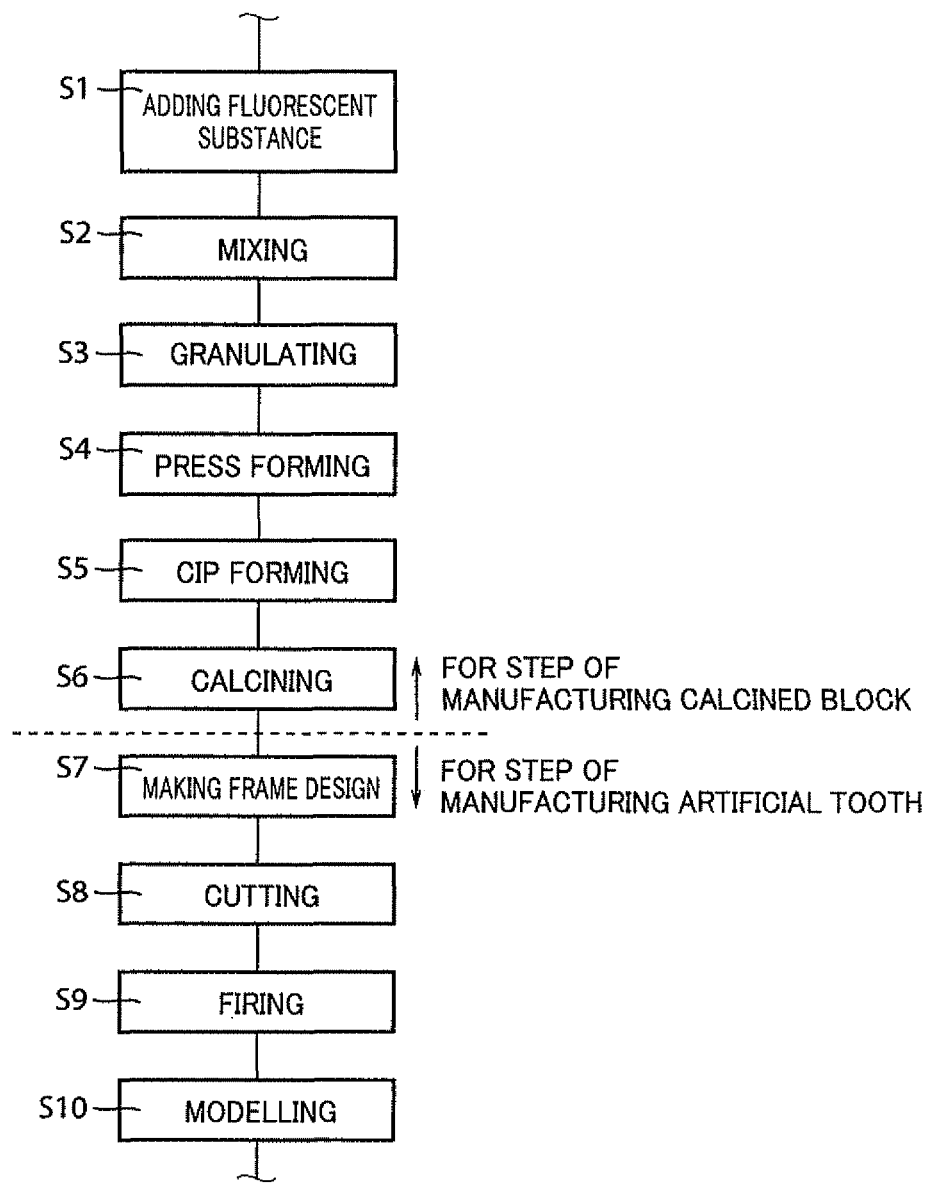
FIG. 4 is a process chart for illustrating a manufacturing method and an approach in the use of the block shown in FIG. 1.

Moreover, the block 10 and the tooth crown 20, employing such a block, can be manufactured in, for instance, a manner as described below. In FIG. 4, at fluorescent substance adding step S1, first, zirconia granules, manufactured using an appropriate synthesizing method and granulation method, are prepared to which $Eu_2O_3$ powder is added in an amount of 0.05 (wt %). These substances are mixed together at mixing step S2 and, subsequently, granulated into raw materials suited for press forming at granulating step S3. These steps are carried out by mixing the substances in a mortar while performing the granulation. In addition, organic high-polymer binder and/or plasticizer are added to the zirconia granules. Moreover, in addition to the fluorescent material, a coloring agent may be added. Besides, in stead of mixing with the use of the mortar, methods may be employed including wet mixing conducted with a ball mill, using solvents such as ethanol or water, etc., and zirconia balls upon which the granulation is carried out using a spray drier.

Next, at press forming step S4, the granulated raw material is formed in a disc-shaped compact body by uniaxial pressing. At succeeding CIP forming step S5, the resulting disc-shaped compact body is subjected to CIP forming under a pressure of, for instance, 100 to 500 (MPa). This step is taken for increasing uniformity of the compact body and, hence, no such step may be implemented if adequate uniformity can be obtained merely by press forming.

At subsequent calcining step S6, the compact body (i.e., a green block) is subjected to calcining treatment. This calcining treatment is performed by raising temperatures to a range from 800 to 900(° C.) and held for about 1 to 6 hours. During such temperature raising procedure, a resin binder agent (binder), contained in such granules, are fired and removed to further proceed the bonding of granules such that the block 10 is obtained as mentioned above.

The following steps include steps to be performed by a dental laboratory and a dental technician and carried out for each patient needed to be mounted with an artificial tooth. At frame designing step S7, the frame is designed at a predetermined division ratio determined for each block 10 by using CAD based on a model provided by a dental doctor.

Next, at cutting step S8, the block 10 is cut out into a frame calcined body by using CAM in accordance with the design mentioned above.

At succeeding firing step S9, the cutout frame calcined body is subjected to firing treatment. This firing treatment is performed by raising temperatures in a range from 1300 to 1600(° C.) to be held for about 30 minutes to 2 hours. This allows the zirconia raw material to be fired, thereby obtaining the frame 14.

At subsequent modeling step S10, a porcelain is modeled on the frame 14. For instance, a slurry, made of ceramic powder dispersed in a propylene glycol aqueous solution or the like, is applied to the frame 14 to form a ceramic layer (i.e., the upper layer 18, etc.) when fired at a temperature of, for instance, 930(° C.). With such step repeatedly conducted depending on needs, a desired artificial tooth (i.e., the tooth crown 20 or the like) can be obtained.

With the present embodiment, firing the frame 14 at the high temperatures ranging from 1300 to 1600(° C.) allows the frame 14, made of zirconia, to have fluorescent property as a result of $Eu_2O_3$ being added enabling the emission of fluorescence when irradiated with the ultraviolet rays as mentioned above. That is, the frame 14, made of zirconia material, can be obtained having fluorescence with traceability. Therefore, the frame 14 has a traceability function due to an ability of emitting fluorescence upon irradiation of the UV lamp or the black light or the like applied to a cross sectional surface when resulted in, for instance, breakage. Due to an effect of fluorescence emission in blue color when irradiated with the black light, further, the frame 14 has the same fluorescent property as that of the upper layer 18 even in an area in which the upper layer 18 is thin or in another area in which no upper layer is provided, resulting in an advantage of having an excellent esthetical effect, With the present embodiment, furthermore, the amount of the fluorescent material added to give fluorescent property is not more than 0.05 (wt %). This results in an advantage with no sacrifice in strength of the zirconia material per se even though no specific data is demonstrated.

Meanwhile, the example of the element, available to give fluorescent property to zirconia, is not only limited to Eu but may preferably include other elements such as Ga and some kinds of rare earths. Table 1, described below, demonstrates results on evaluations made on fluorescent property or the like of test pieces prepared with other rare earth oxides or the like being added in place of $Eu_2O_3$ to the zirconia raw material. Each test piece was prepared by preparing the raw material to which the rare earth oxides or the like are added in an amount indicated in the Table in fluorescent substance adding step S1 to prepare granulated raw materials that were press formed into a compact body to be subjected to firing treatment at a temperature of 1400(° C.). In Table 1 listed below, a column "black light" and a column "UV lamp" indicate brightness of fluorescence when irradiated therewith respectively with relative numerical values of 0 to 6 in terms of "5" of fluorescence of a porcelain material conventionally used for prostheses and in terms of "0" of fluorescence in non-observation. The black light had a radiation wavelength of approximately 365 (nm) and the UV lamp had a radiation wavelength of approximately 254 (nm). In addition, a column "body color" represents a color tone under a visible light.

TABLE 1

| | Fluorescent Substance | | Black | UV | |
|---|---|---|---|---|---|
| No. | Kind | Content(wt %) | Light | Lamp | Body Color |
| 1 | $Pr_2O_3$ | 1 | 0 | 1 | Brown |
| 2 | $Sm_2O_3$ | 1 | 4 | 1 | White |
| 3 | $Eu_2O_3$ | 1 | 4.5 | 6 | White |
| 4 | $Eu_2O_3$ | 0.5 | 4 | 4 | White |
| 5 | $Eu_2O_3$ | 0.1 | 3 | 3.5 | White |
| 6 | $Eu_2O_3$ | 0.05 | 2.5 | 2.5 | White |
| 7 | $Eu_2O_3$ | 0.01 | 1.5 | 1.5 | White |
| 8 | $Ga_2O_3$ | 1 | 1 | 1 | White |
| 9 | $Gd_2O_3$ | 1 | 1 | 1 | White |
| 10 | $Tm_2O_3$ | 1 | 1 | 1 | White |
| 11 | $Nd_2O_5$ | 1 | 1 | 1 | White |
| 12 | $Dy_2O_3$ | 1 | 4 | 1 | White |
| 13 | $Tb_4O_7$ | 1 | 1 | 4 | Orange |
| 14 | $Er(CH_3COO)_3$ | 1 | 1.5 | 1 | Light Pink |

As indicated in Table 1 listed above, a test piece 1, added with Pr, had a body color changed to a brown color with emission peaks appeared in wavelength of 365 (nm), 468 (nm), 486 (nm) and 614 (nm) when excited with the UV lamp irradiation of a wavelength of 254 (nm). No emission peak was present with the black light having the wavelength of 365 (nm). The florescent light was emitted but a remarkable change of the body color, occurred to be unsuitable for use.

With a test piece 2 added with Sm, further, fluorescence was emitted in color from yellow to orange with a relatively high brightness when irradiated using the black light but a brightness caused by the UV light remained in a relatively low value. In addition, more particularly, the florescent light had emission peaks in the wavelengths of 365 (nm), 395 (nm), 451 (nm), 468 (nm) and 573 (nm) when excited with the UV lamp irradiation of the wavelength of 254 (nm), and had emission peaks in the wavelengths of 573 (nm) and 622 (nm) with the black light of the wavelength of 365 (nm). Since no change took place in body color, this may have an application desired for the florescent light to be emitted with the black light and may be employed when a low brightness will suffice.

Test pieces Nos. 3-7, to which Eu was added, had an added amount varied in a range from 1 to 0.01 (wt %). The addition of such an element in an extremely small amount even as low as 0.01 (wt %) resulted in light emissions with adequately high brightness even when irradiated with any of the black light and the UV lamp. It was recognized that there was a tendency where the brightness will be high in exposure to any of such lights as the added amount increases. In case of the black light, fluorescence was emitted in blue color and, in case of the UV lamp, fluorescence emission occurred in the blue color. When excited with the UV lamp irradiation at the wavelength of 254 (nm), more particularly, the emission peaks occurred at the wavelengths of 366 (nm), 397 (nm), 451 (nm), 468 (nm), 591 (nm) and 605 (nm). With the irradiation of the black light at the wavelength of 365 (nm), the emission peak occurred at the wavelength of 372 (nm). Further, no variation of the body color was confirmed. Furthermore, the brightness, resulting from irradiation of the UV lamp, i.e., the brightness occurring when excited at the wavelength of 254 (nm), resulted in a slightly higher result. In addition, relative to the case of adding Sm, even the very small added amount makes it possible to obtain higher brightness. Thus, it can be said that, in order to eliminate a likelihood of suffering the occurrence of damage to inherent characteristics of the material in nature by decreasing impurities, added to zirconia material, to be minimized as little as possible, Eu is a more preferable fluorescent material.

Further, all of test pieces Nos. 8-11, to which Ga, Gd, Tm and Nd were added, were recognized that the emissions of fluorescence occurred each in blue color when irradiated with any of the black light and the UV lamp with brightness remained to be low in any case. More particularly, the addition of Tm resulted in emission peaks at the wavelengths of 365 (nm), 396 (nm), 450 (nm), 468 (nm) and 483 (nm) when excited with the UV lamp irradiation at the wavelength of 254 (nm) and an emission peak occurred at the wavelength of 460 (nm) with the black light at the wavelength of 365 (nm). Further, no variation of body color was present.

Furthermore, a test piece No. 12, to which Dy was added, was recognized to have light emissions with high brightness when irradiated with the black light. Although the light emissions were recognized in multiple colors including blue, yellow and orange, etc., orange-colored light emission was intensive with the resultant occurrence of light emissions in bright and light orange as a whole. Moreover, even when irradiated with the UV lamp, light emission occurred even in low brightness. More particularly, when excited with the UV lamp irradiation at the wavelength of 254 (nm), emission peaks occurred at the wavelengths of 365 (nm), 397 (nm), 451 (nm), 468 (nm), 483 (nm) and 583 (nm) and, in the irradiation of the black light at the wavelength of 365 (nm), emission peaks occurred at the wavelengths of 484 (nm), 497 (nm) and 584 (nm). Further, no variation of body color was present.

Moreover, a test piece No. 13, to which Tb was added, was recognized to have a body color changed to an orange color but to have light emission with high brightness when irradiated with the UV lamp. Although the light emissions occurred in multiple colors, a blue color was slightly strong with other weakened light emissions being present in yellow and orange. In addition, a light emission occurred but in low brightness even when irradiated with the black light. In particular, when excited with the UV lamp irradiation at the wavelength of 254 (nm), emission peaks occurred at the wavelengths of 365 (nm), 468 (nm), 489 (nm), 557 (nm), 584 (nm) and 621 (nm).

Further, a test piece No. 14, to which Er was added, was recognized that a body color changed to a thin pink color but fluorescent emission occurred in blue color. However, the brightness was low and the brightness, appeared when irradiated with the black light, was slightly higher than that obtained when irradiated with the UV lamp. In this case, Er was added in a form of acetate tetrahydrate.

Besides, it becomes possible to replace rare earth oxides or the like to those generally used as fluorescent materials for permitting the zirconia material to have fluorescent property. Table 2, listed below, indicates evaluation results on fluorescent property of prepared test pieces in which various fluorescent substances are added to the zirconia material. In Table 2, a column "Mixing" represents a mixing method for zirconia material and fluorescent powder and "Wet type" represents wet mixing using ball mills. In addition, two temperatures, indicated in a column "Black Light" and a column "UV Lamp", respectively, represent firing temperatures of the test pieces.

TABLE 2

| | Fluorescent Substance | | | Black Light | | UV Lamp | | |
|---|---|---|---|---|---|---|---|---|
| No. | Kind | Content(wt %) | Mixing | 1350(° C.) | 1400(° C.) | 1350(° C.) | 1400(° C.) | Body Color |
| 15 | $Y_2SiO_5$: Ce | 1 | Mortar | 3 | 1 | — | — | White |
| 16 | $Y_2SiO_5$: Ce | 3 | Mortar | 3.5 | 1 | 1 | 1 | White |
| 17 | $Y_2SiO_5$: Ce | 5 | Mortar | 4 | 2 | 2 | 2 | White |
| 18 | $Y_2SiO_5$: Tb | 3 | Mortar | 3 | 3 | 4 | 4 | Light Orange |
| 19 | $(Y,Gd,Eu)BO_3$ | 3 | Mortar | 3 | 3 | 4 | 4 | White |
| 20 | $Zn_2SiO_4$: Mn | 3 | Mortar | 0 | 0 | 0 | 0 | Gray |
| 21 | $Y_2O_3$: Eu | 3 | Mortar | 3 | 3 | 4 | 4 | White |
| 22 | YAG: Ce | 3 | Mortar | 4 | 4 | 3 | 3 | Yellow |
| 23 | $ZnGa_2O_4$: Zn | 0.05 | Wet Type | 1 | 1 | 1 | 1 | White |
| 24 | $BaMgAl_{10}O_{17}$: Eu | 0.05 | Wet Type | 1.5 | 1.5 | 4 | 4 | White |
| 25 | $ZnGa_2O_4$: Mn | 0.05 | Wet Type | 0 | 0 | 0 | 0 | Gray |
| 26 | $BaMgAl_{10}O_{17}$: EuMn | 0.05 | Wet Type | 0 | 0 | 0 | 0 | Gray |

In Table 2 listed above, $Y_2SiO_5$:Ce, added to test pieces Nos. 15 to 17, represents a generally used fluorescent substance that has been added to the porcelain in the related art with a view to adjusting color tones or the like. This allowed the emission of fluorescence in blue color and, when added in an amount of 1 (wt %), the fluorescence emission occurred to some extent when irradiated with the black light but no fluorescence emission could be obtained upon irradiation of the UV lamp. The addition of such substance in an amount of 3 (wt %) resulted in fluorescence emission with improved brightness and caused fluorescence emission to occur even when excited with the UV lamp irradiation. Adding such a substance in an amount of 5 (wt %) resulted in further improved brightness. More particularly, when excited with the UV lamp irradiation at the wavelength of 254 (nm), emission peaks occurred at wavelengths of 365 (nm), 396 (nm), 450 (nm), 468 (nm) and 517 (nm) whereas with the black light at the wavelength of 365 (nm), the emission peaks occurred at the wavelengths of 372 (nm) and 433 (nm). In addition, no variation took place in body color.

Test piece No. 18, added with $Y_2SiO_5$:Tb, had a body color changed to be light orange but fluorescence emission occurred with high brightness. In any of the black light irradiation and the UV lamp irradiation, the high brightness occurred but the latter case achieved in a higher result.

With test piece No. 19, added with $(Y, Gd, Eu)BO_3$, and test piece No. 21, added with $Y_2O_3$:Eu, further, fluorescence emission occurred in pink color with high brightness upon irradiation of the UV lamp. Even when irradiated with the black light, high brightness was obtained but in a slightly low level. In any cases, no change of body color occurred.

With test piece No. 20 added with $Zn_2SiO_4$:Mn, no fluorescence emission occurred even when irradiated with any of the black light and the UV lamp. In addition, body colors had a change in gray.

With test piece No. 22 added with YAG:Ce, fluorescence emission occurred in green color when excited with the ultraviolet ray irradiation but the black light irradiation resulted in higher brightness than that resulted when irradiated with the UV lamp. In addition, a body color had a change to yellow color.

With test piece No. 23, added with $ZnGa_2O_4$:Zn, which included fluorescent substance material mixed by wet mixing, fluorescence emission occurred in blue color but with low brightness when irradiated with any of the black light and the UV lamp. In addition, no change of body color was recognized.

With test piece No. 24, added with $BaMgAl_{10}O_{17}$:Eu, which included fluorescent substance material mixed by wet mixing, fluorescence emission occurred in blue color with extremely high brightness when irradiated with the UV lamp. Even when irradiated with the black light, fluorescence emission occurred in blue color but with a lower brightness than that of the former result. No change of body color was recognized.

None of test piece No. 25, added with $ZnGa_2O_4$:Mn and test piece No. 26, added with $BaMgAl_{10}O_{17}$:EuMn, had no fluorescence emission. In both cases, body colors had changes in gray.

While the present invention has been described above with reference to the accompanying drawings, it is to be construed that the present invention can be implemented in other modes and that various modifications can be made within a scope of the present invention without departing from the spirit of the invention.

NOMENCLATURE OF ELEMENTS

10: zirconia block
12: outline of the frame to be cut out
14: frame
16: surface
18: upper layer
20: tooth crown

The invention claimed is:

1. A fluorescent zirconia material comprising a fluorescent component including a fluorescent material that includes $Y_2SiO_5$:Ce;
   the fluorescent component being capable of emitting fluorescence when subjected to a firing treatment at temperatures ranging from 1300 to 1600(° C.) under oxidizing environments;
   the fluorescent zirconia material being material for a frame of a dental prosthesis; and the fluorescent component emitting a predetermined fluorescence when excited with a light of a predetermined wavelength.

2. The fluorescent zirconia material according to claim 1, wherein the predetermined wavelength is a wavelength of ultraviolet rays equal to or greater than 300(nm) with the fluorescence being provided in blue color and blue-white color.

3. The fluorescent zirconia material according to claim 1, wherein the predetermined wavelength is a wavelength of ultraviolet rays equal to or less than 300(nm).

* * * * *